United States Patent [19]

Williams et al.

[11] Patent Number: 4,613,517

[45] Date of Patent: Sep. 23, 1986

[54] HEPARINIZATION OF PLASMA TREATED SURFACES

[75] Inventors: Joel L. Williams, Cary; Terry S. Dunn, Raleigh; James P. O'Connell, Chapel Hill; David Montgomery, Cary, all of N.C.

[73] Assignee: Becton, Dickinson and Company, Franklin Lakes, N.J.

[21] Appl. No.: 764,809

[22] Filed: Aug. 12, 1985

Related U.S. Application Data

[63] Continuation of Ser. No. 641,421, Aug. 17, 1984, abandoned, which is a continuation of Ser. No. 488,911, Apr. 7, 1983, abandoned.

[51] Int. Cl.$^4$ .................................................. A01N 1/02
[52] U.S. Cl. .......................................... 427/2; 427/40; 427/41; 424/78
[58] Field of Search ............... 427/2, 40, 41, 430.1; 424/183, 78, 83; 514/56; 264/83, 85

[56] References Cited

U.S. PATENT DOCUMENTS

| | | | |
|---|---|---|---|
| 3,415,683 | 12/1968 | Coffman et al. | 204/168 X |
| 3,453,194 | 7/1969 | Bennett et al. | 204/159.12 |
| 3,457,098 | 7/1969 | Leininger et al. | 424/183 X |
| 3,518,108 | 6/1970 | Heiss et al. | 204/170 X |
| 3,634,123 | 1/1972 | Eriksson et al. | 424/183 X |
| 3,663,265 | 5/1972 | Lee et al. | 117/93.1 GD |
| 3,776,762 | 12/1973 | Bernath | 117/93.1 GD |
| 3,810,781 | 5/1974 | Eriksson et al. | 424/183 X |
| 3,826,678 | 7/1974 | Hoffman et al. | 424/35 X |
| 3,846,353 | 11/1974 | Grotta | 424/183 X |
| 4,072,769 | 7/1978 | Lidel | 427/38 |
| 4,091,166 | 5/1978 | Kubacki | 428/411 |
| 4,326,532 | 4/1982 | Hammer | 427/339 X |
| 4,344,981 | 8/1982 | Imada et al. | 427/40 |
| 4,349,467 | 9/1982 | Williams et al. | 525/54.2 |
| 4,364,970 | 12/1982 | Imada et al. | 427/40 |

OTHER PUBLICATIONS

Gott, Vincent L. et al., *Heparin Bonding on Colloidal Graphite Surfaces*, Science, vol. 142, pp. 1297–1298, Apr. 25, 1963.

Falb, R. D., *Surface-Bonded Heparin*, Polymers in Medicine and Surgery, pp. 77–86, Plenum Press, N.Y., 1975.

*Primary Examiner*—Norman Morgenstern
*Assistant Examiner*—K. Jaconetty
*Attorney, Agent, or Firm*—Richard E. Brown

[57] ABSTRACT

The disclosure is of a method to improve the antithrombogenicity which results when heparin is attached to a polymeric surface. The polymeric surface is activated by treatment with a plasma. The surface thus activated is rendered receptive to the binding of a surface active agent. The surface active agent in turn reacts with heparin to provide a polymeric surface of exceptional antithrombogenicity when contacted with blood for an extended period of time.

29 Claims, No Drawings

HEPARINIZATION OF PLASMA TREATED SURFACES

This application is a continuation of application Ser. No. 641,421, filed Aug. 17, 1984, which is a continuation of Ser. No. 488,911, filed Apr. 27, 1983, both now abandoned.

BACKGROUND OF THE INVENTION

1. Field of the Invention

The present invention relates generally to methods of reducing thrombogenicity associated with polymer resin articles. More particularly, the present invention relates to a method for producing a heparin coated polymeric article wherein the polymeric article is treated with a plasma prior to attachment of the heparin.

2. Description of Prior Art

U.S. Pat. No. 3,846,353, to Grotta indicates that polymers, both natural and synthetic and particularly certain synthetic plastics have come to the fore as preferred materials for prosthetic devices. Their major drawback, however, is their thrombogenicity. Even though plastics are used in various apparatus such as heart-lung machines, kidney machines, and artificial heart valves and patches, the tendency of these materials to cause coagulation necessitates the use of anticoagulants such as heparin. Even such plastics as Teflon (polytetrafluoroethylene) and the silicone rubbers which are more compatible with blood than most plastics, still show thrombogenic characteristics. The first real advance in the preparation of nonthrombogenic materials was described by Dr. Vincent Gott. The method used by Dr. Gott comprised treating a graphited surface first with Zephiran (benzalkonium chloride) and then with heparin. Materials treated in this way were nonthrombogenic in vivo for long periods of time. The major disadvantage, however, with these materials, was that the method could only be practiced on rigid plastics and a need still exists for a suitable flexible nonthrombogenic plastic, as well as a method of producing the same.

Various methods have been devised for introducing antithrombogenicity which involve chemically bonding a quaternary ammonium salt to the polymeric surface and then heparinizing the thus modified surface. Illustrative of these methods are the procedures described in U.S. Pat. No. 3,634,123 to Eriksson wherein an article having a plastic surface is heated to near or above its softening point in an aqueous solution of a cationic surface active agent, as, for example, long chain alkylamine hydrohalides. In such manner, the surface active agent permeates and thereby becomes affixed to the resin surface. In addition, the hydrocarbon portion of the surface-active agent is thought to become bound to the surface of the plastic. Subsequent digestion of the plastic articles with an aqueous solution of heparin provides articles of enhanced antithrombogenicity.

A further improvement is described in by U.S. Pat. No. 3,810,781 to Eriksson, wherein heparinized plastic surfaces are stabilized by cross linking the bonded heparin molecules with dialdehydes. By this procedure, while some improvement in stability results, not all of the bonded heparin is impervious to desorption by washing.

The binding of substantially greater quantities of heparin to the polymer surface is described in U.S. Pat. No. 4,349,467 to Dudley, wherein the step of heparinization is carried out with aqueous solutions of heparin of 5% or greater concentration. Using this procedure, up to 18 ug/cm of heparin are bound to a polyurethane surface through the surface active agent.

Many of the drawbacks and disadvantages of earlier methods for rendering polymeric surfaces non-thrombogenic are eliminated by the teaching of the above named patents. There remains, however, a need for methods to adhere higher quantities of heparin, impervious to desorption, to polymeric surfaces for use in articles which will be in contact with blood for prolonged periods of time. These needs are met by the method of the current invention incorporating a plasma treatment of the resin surface before the heparinization step.

The process of formation of a plasma by electromagnetic activation of a gas by either a glow discharge or a corona discharge, and the use of such plasma for activating polymeric surfaces is known to accomplish various purposes. For example, U.S. Pat. No. 3,663,265 to Lee teaches deposition of vaporized polymeric material onto substrate surfaces by treatment of the polymeric material with a plasma from an inert gas whereby the polymer is vaporized and contacted with the substrate to form the coating. In U.S. Pat. No. 4,091,166 to Kubacki, a plastic surface is treated with a plasma of boron trifluoride, optionally admixed with an organic monomer to deposit a boron trifluoride containing coating. U.S. Pat. No. 3,415,683 to Coffman discloses formation of deposits from organic materials on substrates such as bare metals in a corona reaction. U.S. Pat. No. 3,518,108 to Heiss teaches formation of polymer coatings from aromatics, aliphatics and silicones in a plasma of inert gas or hydrogen.

U.S. Pat. No. 3,776,762 to Bernath teaches glow discharge deposition of fluorocarbon polymeric coatings onto metallic or non-metallic surfaces by passing DC current through a low pressure atmosphere of the monomer. U.S. Pat. No. 4,326,532 to Hammar discloses the use of a plasma for priming the surface of a polymeric resin for deposition of a coating of chitosan receptive to subsequent heparin binding.

SUMMARY OF INVENTION

The invention comprises a method to improve adherence of heparin to a polymeric surface. The polymeric article heparinized according to the present invention has improved compatibility with blood due to the increased level of heparin that can be adhered to the surface. The improvement results from a plasma treatment of the plastic surface before the heparinization step. The plasma is generated by ionization of a gas at low pressure by a radio frequency discharge. The frequency and power used to generate the plasma and the time of plasma treatment are variable over wide ranges. The plasma-treated polymeric surface thus obtained is subjected to heparinization according to known methods whereby up to 10 fold more heparin is bound to the polymeric surface than occurs with untreated polymers. In addition, the heparin is bound more firmly, affording highly durable heparin surfaces which are resistant to removal of the heparin by such operations as washing or rubbing. Another advantage of the present invention is that no effect on the mechanical or penetration characteristics of prosthetic devices such as catheters is seen. Furthermore, in contrast to prior art methodology, the process of the present invention is inexpensive and clean.

DETAILED DESCRIPTION OF THE INVENTION

The polymeric resin materials which serve as the substrate to be treated by the method of this invention may be any polymeric resin, natural or synthetic, conventionally used to fabricate articles commonly used in contact with blood. For example, catheters, artificial blood vessels, valves and like prosthetics are frequently fabricated from polyethylene, polacrylics, polypropylene, polyvinyl chloride, polyamides, polyurethanes, polyvinylpyrrolidone, polyvinyl alcohols, cellulose acetate, polystyrene, polytetrafluoroethylene, polyesters such as polyethylene terephthalate, silicone rubber, natural rubber, polycarbonates and like polymeric resins and hydrogels, thereof. The resin substrate may be rigid or flexible in character, cellular or non-cellular, porous or non-porous. Also within the scope of the invention are metal or ceramic materials coated with polymer resins such as described above.

The polymeric resin substrate may be first formed into any desired shape, sized or configuration. Representative of such are valves, pins, containers, sleeves, connectors, medical-surgical tubing, prosthetic devices and the like of any size. Alternatively, the polymeric resin may be first treated by the method of this invention and subsequently fabricated into the desired shape.

In accordance with the method of this invention, the polymeric resin substrate is subjected to a plasma treatment before heparinization. This plasma treatment may be carried out in any plasma generator, as, for example, those described in U.S. Pat. No. 3,847,652. The plasma may be generated from a variety of gases or mixtures thereof. Gases frequently used include hydrogen, helium, ammonia, nitrogen, oxygen, neon, argon, krypton and xenon. Gas pressures are advantageously maintained at 5 mm of Hg or below, preferably from about 0.1 to about 1.0 mm of Hg, in order to benefit from reduced voltage requirements.

A wide range of power settings, radio frequencies and durations of exposure of the polymeric surface to the plasma may be used. Ranges for these three parameters which provide advantageous results are DC or AC power levels up to about 200 watts, from about 1 to about 50 megahertz and from about 0.1 to about 30 minutes, respectively. Preferred ranges are 10–50 watts, 10–20 megahertz and 2–10 minutes, respectively.

To the plasma surface thus activated by the plasma treatment there is affixed by absorption on the surface thereof a quarternary ammonium salt of the general formula I

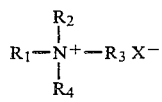

wherein $R_1$ is alkyl of 12–18 carbon atoms, $R_2$, $R_3$ and $R_4$ are each independently selected from the group consisting of hydrogen and lower alkyl of 1 to 6 carbon atoms, and X is a negative monovalent ion, such as halogen. In preferred embodiments of this invention, the group $R_2$ is lower alkyl and $R_3$ and $R_4$ are hydrogen. In a particularly preferred embodiment, $R_2$ is methyl, $R_3$ and $R_4$ are hydrogen and X is chlorine.

The compound of Formula I is affixed to the polymeric resin substrate by permeating the compound throughout the molecular structure of the resin substrate, i.e., by chemisorption. While not willing to be bound by anything, it is believed that the $C_{12}$ to $C_{18}$ alkyl chain portion of the compound of formula I may also bind to the polymeric resin substrate which has been chemically altered by the plasma treatment. The compound I may be chemisorbed into the polymeric resin substrate by steeping the substrate in a dispersion of the compound I. In this steeping operation, the concentration of compound I is not critical, but is advantageously maintained within the range of 0.01% to 2.0% by weight. Steeping may be carried out at ambient or at elevated temperatures up to or slightly above the softening point temperature for the resin substrate. By the term "softening point temperature" we mean the temperature at which the surface of the resin substrate becomes pliable due to the additional mobility of the substrate molecules. Following fixation of the quarternary ammonium salt compound I to the surface of the polymeric resin substrate, excess compound I may be removed by washing with distilled water or saline solutions.

The polymeric resin substrate bearing the affixed quarternary ammonium salt on its surface is then "heparinized" by immersion in an aqueous solution of sodium heparin. The temperature at which immersion is advantageously carried out is within the range of from about room temperature to about 80° C., but less than the softening point temperature for the resin substrate. The length of immersion is dependent on the temperature used, but is generally long enough to permit the substrate to pick up at least about 0.1 International Unit per square centimeter of substrate surface. At a temperature of about 70° C., for example, this is usually accomplished in about 1 hour, using a heparin solution with a concentration of from about 1% to about 15%, preferably from about 8 to about 10%, of sodium heparin. (As used herein, all percentages are by weight unless indicated otherwise.) During heparinization the negative ion of the sodium heparin complexes with the positive ion of the compound I according to the scheme:

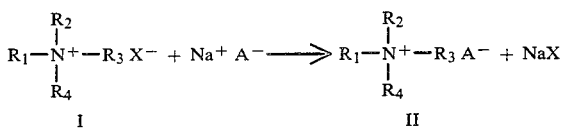

wherein A represents the active heparin moiety, that is, the negative ion of a salt of heparin and $R_1$, $R_2$, $R_3$, $R_4$ and X are as previously defined.

Following the heparinization step, the polymeric resin is removed from the heparin solution and rinsed thoroughly with distilled water.

The heparinized surface of the polymeric resin is stabilized toward desorption in the presence of blood by treatment with dialdehydes to cross link functional groups of heparin. This cross linking of functional groups in different heparin units is accomplished when the heparinized surface is digested with aqueous solutions of a dialdehyde over a concentration range of 0.1% to 5.0%. It is most advantageous to maintain contact between the heparinized surface and the dialdehyde solution for a time period of about 1 to about 6 hours at a temperature of ambient to about 80° C. The heparinized surface thus stabilized is removed from the bath, washed thoroughly with distilled water and dried before being brought into contact with blood.

In a preferred embodiment of the present invention, a polytetrafluoroethylene or polyethylene substrate is maintained in an oxygen plasma generated at 13.56 MHz and 50 watts for 10 minutes. The activated substrate is then steeped for 16 hours at 65° C. in an aqueous 15% solution of dodecylmethyl ammonium chloride. After washing with distilled water, the substrate with its affixed quarternary ammonium salt is treated at 65° C. for 16 hours with a 9% solution of sodium heparin. After washing with distilled water, the stabilization step is carried out with a 1% aqueous solution of glutaraldehyde at 60° C. for 2 hours.

The amount of heparin bound to the surface of the polymeric resin substrate is determined by the following method based on the quantitative removal of the dye Azure A by the reactive sites of the bound heparin. Heparinized polymeric substrate of known surface area (between 2 and 35 $cm^2$) is exposed to 5 ml of a 0.001% aqueous solution of Azure A for 45 minutes at 25° C. The quantity of dye removed from the solution is determined by spectrophotometric readings made at 630 nm, with a light path of 1 cm. The dye removed is converted to equivalent amounts of heparin by means of a standard curve prepared by reacting graded amounts of heparin (1–100 micrograms) with five ml of 0.001% Azure A in water, removing the insoluble heparin dye complex by extraction with four ml of cyclohexane, and quantifying the amounts of dye removed spectrophotometrically. The standard curve is then prepared by plotting amount of heparin added versus absorbance at 630 nm. The amount of heparin present on the tubing can then be determined by dividing the amount of heparin removed (derived from the standard curve) by the total surface area of the sample.

Polytetrafluoroethylene articles heparinized according to the method of the present invention were tested for blood compatibility by the procedure described in U.S. Pat. No. 4,367,749, which has a common assignee with the instant patent application.

The following examples are provided to further illustrate the advantages of this invention, but the conditions and materials used and the amounts thereof are not to be construed in any way as limiting of the scope of the invention.

EXAMPLE 1

One hundred 1¼" radiopaque polytetrafluoroethylene catheters weighing 20 g. each were placed in a plasma generator. The system was evacuated for 6 min. to a pressure of 120 u of Hg, then an oxygen bleed was started and maintained for 1 min. at a pressure of 180 u of Hg. A plasma was initiated and maintained at 13.56 MHZ and 50 watts power for 10 minutes. The chamber was air quenched, opened, and the catheters heparinized according to the following sequential 3-step procedure.

(1) Steeping in a 15% aqueous solution of dodecamethylmethyl ammonium chloride, ph 7.5, 16 hours, 65° C., followed by thorough rinsing in distilled water and drying with nitrogen.

(2) Digestion in a 9% aqueous solution of sodium heparin for 16 hours at 65° C., followed by thorough rinsing with distilled water and drying with nitrogen.

(3) Submersion in a 1% aqueous solution of glutaraldehyde for 2 hours at 60°, followed by thorough rinsing with distilled water, 5% aqueous Triton×405, and distilled water. The catheters were dried with nitrogen and stored in a vacuum oven at 25° C.

EXAMPLE 2

A polystyrene microtiter was placed in a plasma generator and the system evacuated to 20μ of Hg. Ammonia was bled in at such a rate that a pressure of 200 of Hg was established and maintained. After a 5 minute flush at this pressure, a plasma was initiated at a frequency of 20 MHZ and 40 watts power. The plasma was maintained for 5 minutes. The radio-frequency was turned off and, after an additional 5 minutes flow of ammonia, the system was opened, the sample removed and heparinized as described in Example 1.

EXAMPLE 3

Twelve polytetrafluoroethylene catheters were placed in the plasma generator. The system was evacuated, and an oxygen bleed of 20 ml per min., giving a pressure of 180μ of Hg was maintained for 2 minutes. A plasma was generated and maintained for 10 min. at 13.56 MHZ and 50 watts poer. The system was quenched with air and the catheters removed and heparinized as in Example 1.

EXAMPLE 4

Polytetrafluoroethylene tubing, 22 gauge, was cut into 3 foot lengths and placed in a glow discharge chamber. The system was evacuated for 5 minutes and flushed with oxygen at 1 mm of Hg for 30 seconds. A flow of oxygen to produce a pressure of 180μ of Hg was initiated, and plasma was generated for 10 minutes at 50 watts and 13.56 MHZ. The system was quenched with air, opened, the substrate repositioned in the chamber to ensure total exposure to the plasma, and the plasma generated a second time in the same way. The tubing was removed from the chamber and heparinized as in Example 1.

EXAMPLE 5

Into a plasma generator were placed the following:
8 20 g., 2½" radiopaque polytetrafluoroethylene catheters (non siliconized)
4 16 g. clear polytetrafluoroethylene catheters
10 16 g. polytetrafluoroethylene guidewires
10 pieces of polytetrafluoroethylene tubing
The chamber was evacuated and an oxygen bleed giving a pressure of 180μ of Hg was maintained for 2 min. A plasma was then initiated using 50 watts of power and a frequency of 13.56 MHZ maintained for 10 min. These materials were heparinized according to the procedure of Example 1. When these materials were exposed to a 0.001% aqueous solution of Azure A, heavy staining occurred, indicating high surface concentrations of heparin.

EXAMPLE 6

Into a plasma generator were placed a group of 2", 2½" and 4" radiopaque polytetrafluoroethylene catheters and 5 polytetrafluoroethylene coated guidewires. These were subjected to an oxygen plasma according to the procedure described in Example 5, and the plasma treated materials were heparinized according to the procedure of Example 1. The heparinized surfaces were subjected to an amount of rubbing equivalent to that which occurs in a typical human insertion. By comparison with samples which were not rubbed, it is seen, based on the Azure A staining procedure, that the heparinized surface retains most of the heparin after rubbing. This indicates a very durable heparin surface.

EXAMPLE 7

This experiment was run in duplicate, giving the results shown in the chart, runs 1 and 2.

Four 4-foot samples each of radiopaque polytetrafluoroethylene tubing and clear polyethylene tubing were subjected to an oxygen plasma generated at 50 watts of power and a frequency of 13.56 MHZ. Treatment durations of 1 and 10 min. and oxygen pressures of 170 u of Hg and 500 u of Hg were used. The samples were heparinized according to the procedure of Example 1, except glutaraldehyde cross linking was not done. The tubing lumens were washed with hot 6 m sodium chloride solution to remove all heparin thereon, since it is desired to quantitate only the heparin on the outer surface of the tubings (which were exposed to plasma). The following chart summarizes the quantities of heparin bound to the surfaces of the tubing.

| SUBSTRATE | oxygen plasma treatment Time Min. | Pressure u of Hg | bound heparin ug cm$^2$ run 1 | run 2 | control* |
|---|---|---|---|---|---|
| polyethylene | 1 | 170 | 5.70 | 6.77 | 7.37 |
| " | 10 | 170 | 5.74 | 6.82 | |
| " | 1 | 500 | 8.71 | 10.30 | |
| " | 10 | 500 | 7.94 | 9.39 | |
| polytetrafluoroethylene | 1 | 170 | 1.24 | 1.50 | 0.22 |
| polytetrafluoroethylene | 10 | 170 | 2.31 | 2.76 | |
| polytetrafluoroethylene | 1 | 500 | 1.66 | 2.01 | |
| polytetrafluoroethylene | 10 | 500 | 4.63 | 5.51 | |

*Heparin bound to substrate not subjected to oxygen plasma.

EXAMPLE 8

Polytetrafluoroethylene tubing of 0.02 mm inside diameter was placed in a plasma generator and the system was evacuated. Nitrogen was bled in at such a rate that a pressure of 180 u of Hg was established and maintained. After a 2 minute flush at this pressure, a plasma was generated and maintained for 10 minutes at 40 watts of power and a frequency of 13.56 MH2. The radiofrequency was turned off and, after an additional 10 minute flow of nitrogen, the system was opened, the samples removed and heparinized as described in Example 1. The articles thus treated with plasma followed by heparinization were compared for blood compatibility with untreated controls and with controls heparinized without plasma treatment. The results of these comparative experiments are shown in Chart II.

Chart II

| Untreated Teflon Controls | Heparinized (no plasma pretreatment) |
|---|---|
| 9.4 minutes | 18 minutes |
| 13.2 | 22 |
| 13.8 | 26 |
| 15.2 | 29 |
| 15.7 | 59 |
| Average = 13.5 minutes | Average = 30.8 minutes |

Heparinized
(with plasma pretreatment)

47 minutes
92
120+ (truncated)

Chart II -continued 136
139

Average = 106.8 minutes

Thus an average 8 fold increase in blood compatibility over untreated controls and a 3–4 fold increase over heparinized articles not pretreated with plasma were achieved.

What is claimed is:

1. In the method of reducing thrombogenicity by attaching heparin to the surface of a polymeric substrate, the improvement comprising subjecting said substrate to a plasma treatment and steeping the plasma-treated substrate with an aqueous dispersion of a cationic surface active agent before attaching said heparin thereto.

2. The improved method in accordance with claim 1 in which said polymeric substrate is selected from the group consisting of silicone, polyethylene, polypropylene, polyurethane, polyacrylics, polyamide, polyester, polyvinyl pyrrolidone, polyvinyl alcohol, cellulose acetate, polyvinylchloride and polytetrafluoroethylene.

3. The improved method in accordance with claim 1 wherein said plasma is generated from a gas selected from the group consisting of oxygen, ammonia, hydrogen, helium, neon, argon, krypton, xenon, nitrogen or mixtures thereof.

4. The improved method in accordance with claim 1 wherein said plasma is generated using a radio frequency discharge.

5. The improved method in accordance with claim 1 wherein said plasma is generated with a power of from about 10 to about 200 watts.

6. The improved method in accordance with claim 1 wherein said polymeric substrate is subjected to said plasma for a period of from about for 0.1 to about 30 minutes.

7. The improved method in accordance with claim 2 wherein said polymeric surface is polytetrafluoroethylene.

8. The improved method in accordance with claim 2 wherein said polymeric surface if polyethylene.

9. The improved method in accordance with claim 3 wherein said gas is maintained at a Chamber pressure of from about 10 to about 300$\mu$ of mercury during generation of said plasma.

10. The improved method in accordance with claim 4 wherein said radio frequency is maintained from about 1 to about 50 megahertz.

11. The improved method in accordance with claim 1 wherein a polytetrafluoroethylene substrate is subjected to an oxygen plasma wherein said plasma is generated by a discharge of about 50 watts at a radio frequency of about 13.56 megahertz, said discharge being maintained for about 10 minutes with said oxygen at a pressure of about 180$\mu$ of Hg.

12. A method for binding heparin to a polymeric substrate comprising the sequential steps of (1) subjecting said polymeric substrate to a plasma treatment, (2) steeping said plasma treated substrate in an aqueous dispersion of a cationic surface active agent, (3) immersing said substrate in an aqueous solution of sodium heparin, and (4) treating said substrate with an aqueous solution of a dialdehyde.

13. The method in accordance with claim 12 in which said cationic surface active agent is a compound of the formula

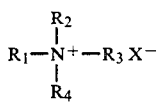

wherein $R_1$ is an alkyl group of 12–18 carbon atoms, $R_2$, $R_3$ and $R_4$ are each independently selected from the group consisting of hydrogen and lower alkyl of 1 to 6 carbon atoms and X is a negative monovalent ion.

14. The method in accordance with claim 13 wherein $R_2$ is a lower alkyl of 1 to 6 carbon atoms, $R_3$ and $R_4$ are each hydrogen and X is halogen.

15. The method in accordance with claim 14 wherein X is chloride.

16. The method in accordance with claim 15 wherein said compound is selected from the group consisting of dodecylmethylammonium chloride, tetradecylmethylammonium chloride, hexadecylmethylammonium chloride, octadecylmethylammonium chloride and dodecylhexylammonium chloride.

17. The method in accordance with claim 16 wherein said compound is dodecylmethylammonium chloride.

18. The method in accordance with claim 12 wherein the aqueous concentration of said cationic surface active agent is from about 0.01 to about 2.0%.

19. The method in accordance with claim 12 wherein the steeping of said substrate in the aqueous dispersion of said surface active agent is carried out for from about 1 to about 24 hours.

20. The method in accordance with claim 12 wherein the steeping of said substrate in the aqueous dispersion of said surface active agent is carried out at ambient temperature or at an elevated temperature up to or slightly above the softening temperature of said substrate.

21. The method in accordance with claim 12 wherein said substrate is immersed in an aqueous solution of from about 1 to about 15 percent of sodium heparin.

22. The method in accordance with claim 12 wherein said immersion is carried out at a temperature from about ambient temperature to about 80° C.

23. The method in accordance with claim 12 wherein said substrate is immersed in said aqueous solution of sodium heparin for from about 1 hour to about 24 hours.

24. The method in accordance with claim 12 wherein said dialdehyde contains from 2 to 6 carbon atoms.

25. The method in accordance with claim 24 wherein said dialdehyde is glutaraldehyde.

26. The method in accordance with claim 12 wherein said dialdehyde is used in an aqueous solution of from about 0.01 to about 5%.

27. The method in accordance with claim 12 wherein said substrate is contacted with said dialdehyde aqueous solution for from about 1 to about 6 hours.

28. The method in accordance with claim 12 wherein the temperature of said dialdehyde aqueous solution is from about ambient temperature to about 80° C.

29. A method for reducing thrombogenicity comprising the sequential steps of:
   (1) subjecting a polytetrafluoroethylene substrate to an oxygen plasma wherein said plasma is generated by a discharge of about 50 watts at a radiofrequency of about 13.56 megahertz, said discharge being maintained for about 10 minutes with said oxygen at a pressure of about $180\mu$ of Hg;
   (2) steeping said substrate in an aqueous solution of dodecylmethyl ammonium chloride of about 15% concentration for about 16 hours at 65° C.;
   (3) washing said substrate thoroughly in distilled water;
   (4) immersing said substrate in an aqueous solution of sodium heparin of about 9% concentration for 16 hours at 65° C.;
   (5) washing said substrate thoroughly in distilled water;
   (6) digesting said substrate in an aqueous solution of glutaraldehyde of about 1% concentration for about 2 hours at about 60° C.;
   (7) washing said substrate in distilled water.

* * * * *